United States Patent [19]
Moore et al.

[11] Patent Number: 6,050,983
[45] Date of Patent: Apr. 18, 2000

[54] SOUND-INSULATED GAS-DIVERTING COLOSTOMY CONTAINER

[76] Inventors: Diane Moore, 1633 Cordwell Dr., Library, Pa. 15129; Frank R. Lancaster, 157 Hamtom Rd., Eighty-Four, Pa. 15330

[21] Appl. No.: 09/179,331

[22] Filed: Oct. 27, 1998

[51] Int. Cl.$^7$ .................................................. A61F 5/44
[52] U.S. Cl. ........................ 604/333; 604/335; 604/337; 128/DIG. 24
[58] Field of Search .................. 604/332–345, 604/327; 128/DIG. 24

[56] References Cited

U.S. PATENT DOCUMENTS

| | | |
|---|---|---|
| 2,064,586 | 12/1936 | Boser . |
| 3,802,436 | 4/1974 | Brondberg . |
| 4,296,749 | 10/1981 | Pontifex . |
| 4,406,657 | 9/1983 | Curutcharry . |
| 5,261,898 | 11/1993 | Polin et al. . |
| 5,348,546 | 9/1994 | Norton ................................... 604/333 |

FOREIGN PATENT DOCUMENTS

| | | | |
|---|---|---|---|
| 0468149 | 9/1950 | Canada .................................. 604/335 |
| 000576181 | 3/1946 | United Kingdom ................... 604/332 |
| 002270725 | 3/1994 | United Kingdom ................... 604/335 |

Primary Examiner—John G. Weiss
Assistant Examiner—Carie Mager
Attorney, Agent, or Firm—Law Offices of K. Patrick McKay, PE, Esq.

[57] ABSTRACT

A colostomy container that is worn by individuals who are in need of a means of passing feces and urine. The container isolates flatus from fecal matter and is capable of containing both excrement elements in separate chambers. Particularly, the stool is collected in a bottom chamber that is disposable, and a spring actuated ball check prohibits reverse flow of fecal matter back into the stoma. The flatus is collected in a top chamber where it is deodorized with a graphite filter and vented. The center of the container is insulated with foam to reduce noise resulting from waste products exiting the stoma and entering the container.

2 Claims, 5 Drawing Sheets

SOUND-INSULATED GAS-DIVERTING COLOSTOMY CONTAINER

BACKGROUND OF THE INVENTION

1. Field of the Invention

The present invention is an accessory for use by individuals who have been inflicted with cancers, stomach or bowel wounds, or other bowel disorders, and who then must rely on an alternate means of removing excrement and gas from the body. The device is a portable and inexpensive, Sound-Insulated Gas-Diverting Colostomy Container. It provides a means of diverting gas from fecal matter while the colostomy bag operates to isolate the colon, intestine, or anus during defecation.

The instant invention is worn by the patients who are in need of a short or long-term means of passing feces and urine. It can be contoured to the body for comfort and easily disposed of and replaced. Lightweight, sound and odor-insulating, and relatively inconspicuous, the container provides the user proper, quiet, and convenient care.

2. Description of the Related Art

The Prior Art encompasses a variety of colostomy and enterostomy related appliances. Also included are accompanying devices developed to improve ostomy care.

Inflictions that necessitate the use of ostomy care are common, and different means of enabling the healing process currently exist. Applications previously have been developed to improve function. Single-chambered devices used to reduce noise from gas emission have stressed the importance of comfort and social rehabilitation. See, e.g., U.S. Pat. No. 4,406,657.

The Prior Art does not include devices which provide a solution to all of the problems that must be overcome for a patient to feel comfortable outside of the hospital environment, while at the same time maximizing function. Specifically, the devices, and combinations thereof, show art restricted to single functionality and/or manual operation in separating gas and solid-liquid fecal matter. Where odor and/or noise control are a factor in previous inventions, patient involvement was necessary in the separation and ridding of gases, assuming gas was excluded from any second chamber. Also, Prior Art inventions which teach sound attenuation do not collaterally serve the purpose of separating gas and solid/liquid matter. In the current art, the passing of a stool required disassembly of the apparatus as fecal matter could produce reverse flow back into the stoma. It is important for those patients who are able to seek care outside of the hospital setting that they get all of the advantages to stoma care, both socially and physically, and with minimum personnel involvement through the use of automatic features. There exists, then, the need for such a device that is encompassed in the present invention, and not in the Prior Art or the reasonable extensions thereof.

PRIOR ART

U.S. Pat. No. 4,296,749 (Pontifer), Oct. 27, 1981, shows a colostomy appliance comprising one pouch for gas collection, and another for solid and liquid waste collection. Closure of each pouch is performed by a central coupling wherein each pouch is automatically closed upon disconnection.

U.S. Pat. No. 5,261,898 (Polin et al.), Nov. 16, 1993, teaches a colostomy apparatus which diverts the fecal stream by direct insertion of a tube into the colon. A disposable bag is secured to the disposal end. Inevitable flow through the tube is achieved by the inflation of an inner balloon that contacts the inner part of the colon, thereby blocking alternative routes through the colon and preventing movement of the tube inward and outward. Slipping is also avoided by the tightening of a retainer ring pressed against the body of the patient.

U.S. Pat. No. 4,406,657 (Curutcharry), Sep. 27, 1983, demonstrates, in the art, a cell porous colostomy device adding optionally an absorbent material, such as activated charcoal. Sound is attenuated by maintaining the shape of the intestinal wall after placement of the device into the intestine. It can be connected to a collecting bag, or secured to the stoma of persons in need of irrigation.

U.S. Pat. No. 2,064,586 (Boser), Dec. 15, 1936, shows a colostomy outfit employing a rigid container with a separable section having inside it a removable bag for disposal.

U.S. Pat. No. 3,802,436 (Brondberg), Apr. 9, 1974, teaches an ostomy bag comprising an adhesive disc secured to the bag and concentric with the opening in the bag. Transverse welding seams distribute the pull caused by the weight of the bag thereby increasing the effectiveness of the adhesion of the bag to the skin.

SUMMARY OF THE INVENTION

The objective of the present invention is to provide a colostomy container that decreases wearer intervention by minimizing the frequency of detaching and reattaching the container to the stoma, thereby limiting the amount of time and attention spent for stoma care.

A secondary objective is to provide features that prohibit reverse flow of fecal matter back into the stoma thereby decreasing the chance of blockage and the number of times necessary for irrigation.

A third objective is to provide features that enable the segregation and discharge of the flatus to occur automatically, thereby requiring less frequent replacement of the colostomy container for gas and/or fecal matter disposal.

A fourth objective is to provide the user the ease of disposing excrement that has seated itself in the bottom chamber of the colostomy container such that less frequent cleaning is necessary.

A fifth objective is to provide a means of reducing the noise made by the emission of flatus and stool as it exits the stoma thereby enabling user confidence in social environments.

A sixth objective is to provide a permanent means of reducing the odor of the emitted gas.

DETAILED DESCRIPTION OF THE PREFERRED EMBODIMENT

The invention will now be described in relation to a preferred embodiment and implementation thereof which is exemplary in nature and descriptively specific as disclosed. As is customary, it will be understood that no limitation of the scope of the invention is thereby intended, and that the invention encompasses such alterations and further modifications in the illustrated device, and such further applications of the principles of the invention illustrated herein, as would normally occur to persons skilled in the art to which the invention relates.

Figure 1:
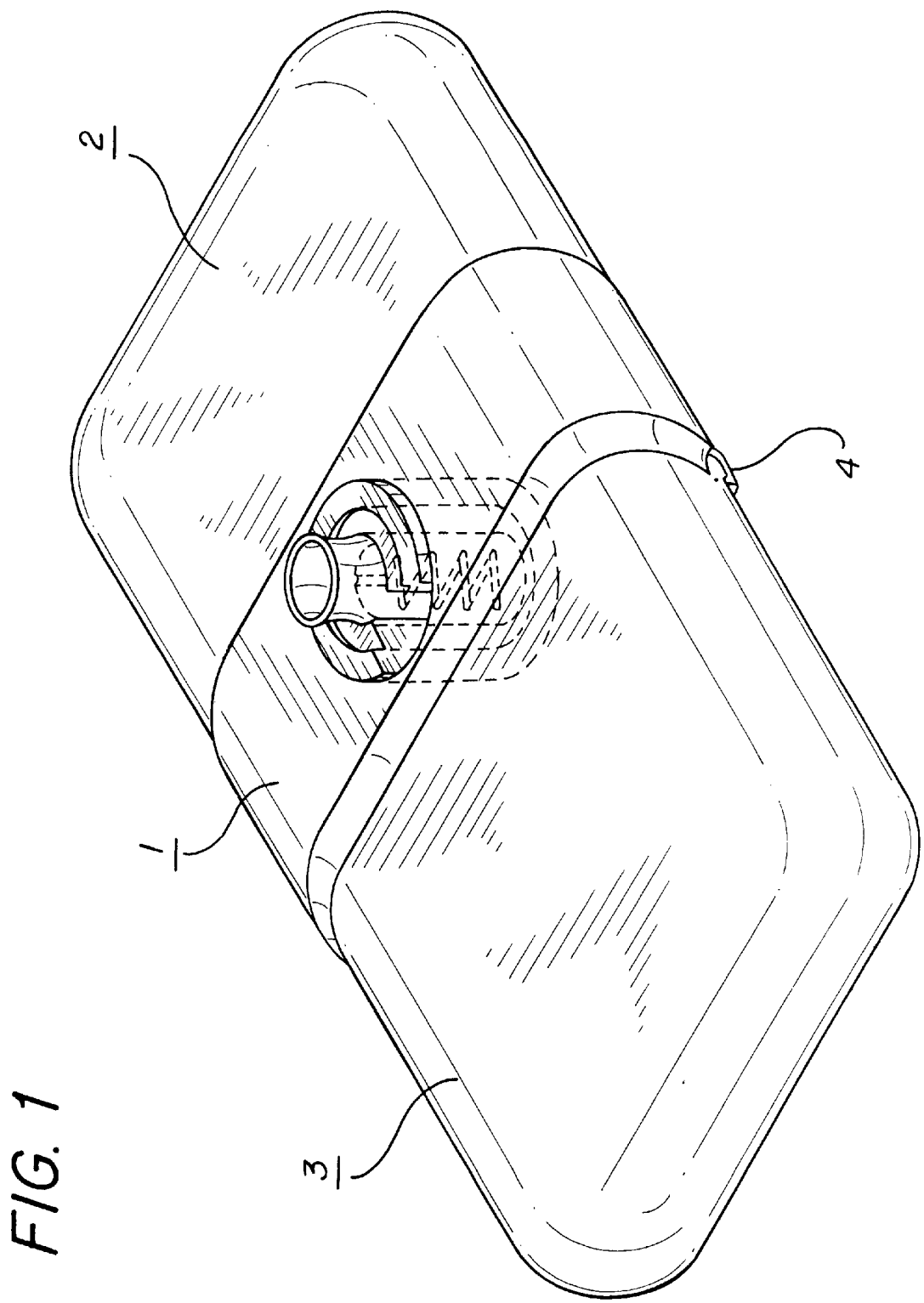
FIG. 1 is a perspective view of the Sound-Insulated Gas-Diverting Colostomy Container showing the constituent sub assemblies.

FIG. 1 shows a perspective view of the Sound-Insulated Gas-Diverting Colostomy Container showing the pertinent subassemblies. The stool-collecting subassembly 3 is removably fastened to the central subassembly 1 by means of the connecting clip 4. The gas-collecting chamber subassembly 2 is fixedly attached to the central subassembly 1.

Figure 2:
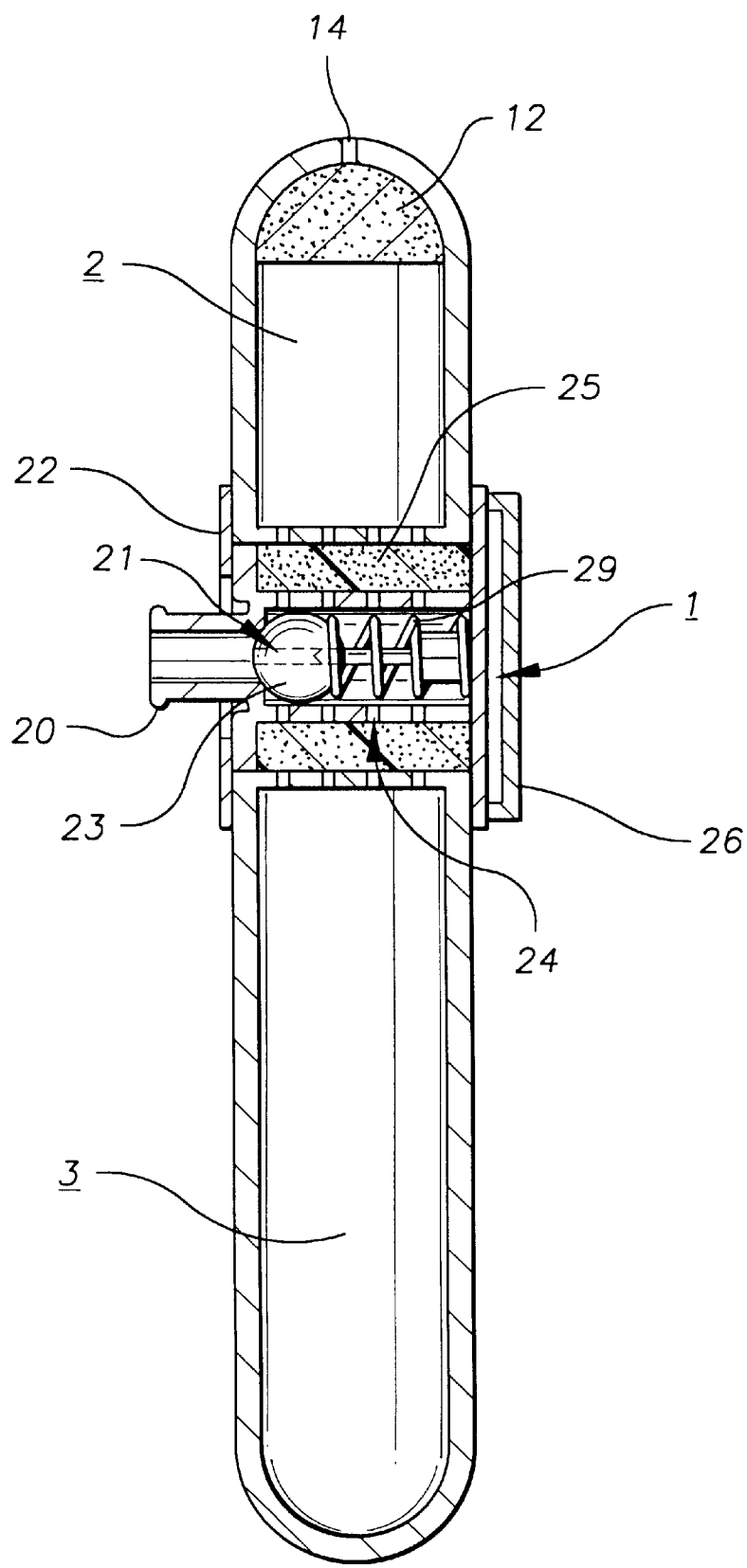
FIG. 2 is a cross-sectional side view of the Sound-Insulated Gas-Diverting Colostomy Container showing the constituent parts.

FIG. 2 shows the Sound-Insulated Gas-Diverting Colostomy Container from the side view. Intestinal or digestively produced gas, preceding any fecal matter, exits the stoma and enters the stoma connection 20, directly attached to the stoma. The gas enters the gas vent path 21 centrally located within the ball check 23 and proceeds through the plurality of gas venting chambers 24 inside the open-cell polyurethane foam 25. The gas is collected in the gas-collecting subassembly 2 and exits through the filtered vent 14 after being filtered by the graphite filter 12 which is fixedly attached to the top of the gas-collecting subassembly 2. Resulting fecal matter enters the container through stoma connection 20. Fecal matter pushes against the ball check 23 and compresses the ball check spring 29. Fecal matter proceeds to fall through the open-cell polyurethane foam 25 and into the stool-collecting subassembly 3. The adhesive donut 22 is removably attached to the central subassembly 1 and encircles the stoma connection 20 as a means for immobilization by the wearer. The belt connector 26 is fixedly attached to the central subassembly 1, wherein a means is produced for fastening the central subassembly 1 to a belt worn by an individual.

Figure 2A:
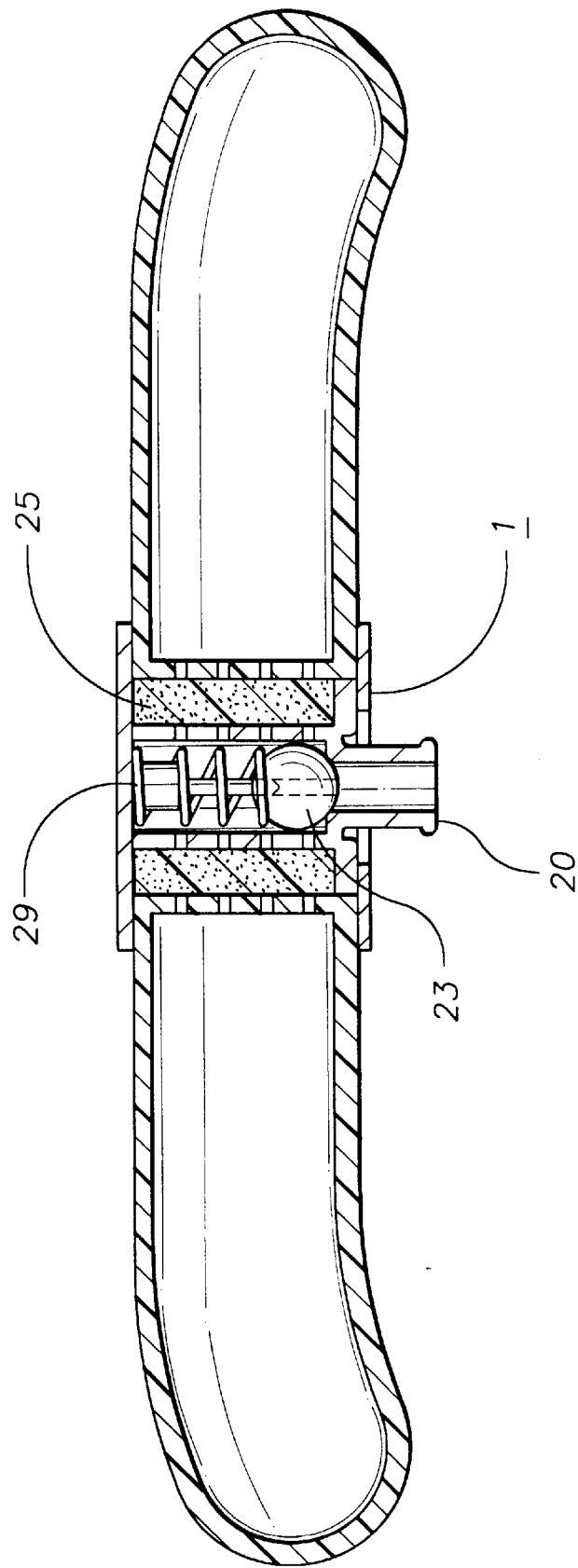
FIG. 2a is a cross-sectional top view of the Sound-Insulated Gas-Diverting Colostomy Container showing a body conforming shape.

FIG. 2a shows the top view of the present invention demonstrating a body conforming shape. A plastic, flexible material could be used to easily shape to the area of the body that employs the use of the invention.

Figure 2B:
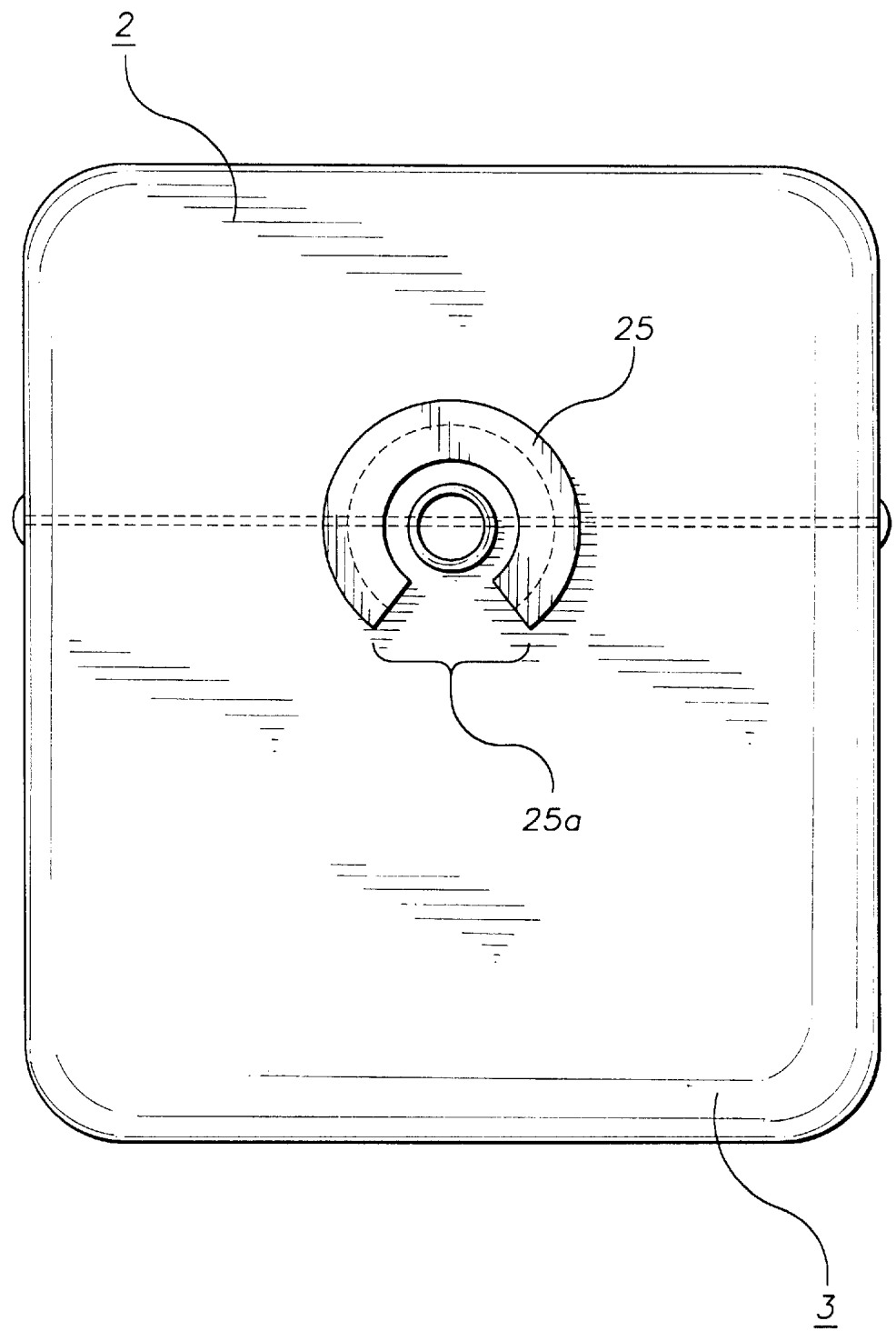
FIG. 2b is a front view of the Sound-Insulated Gas-Diverting Colostomy Container showing a bottom cut-out in the central subassembly.

FIG. 2b shows a front view of the Sound-Insulated Gas-Diverting Colostomy Container with the open-cell polyurethane foam 25 having a cut-out bottom 25a through where stool will pass and fall into the stool-collecting subassembly 3.

Figure 3:
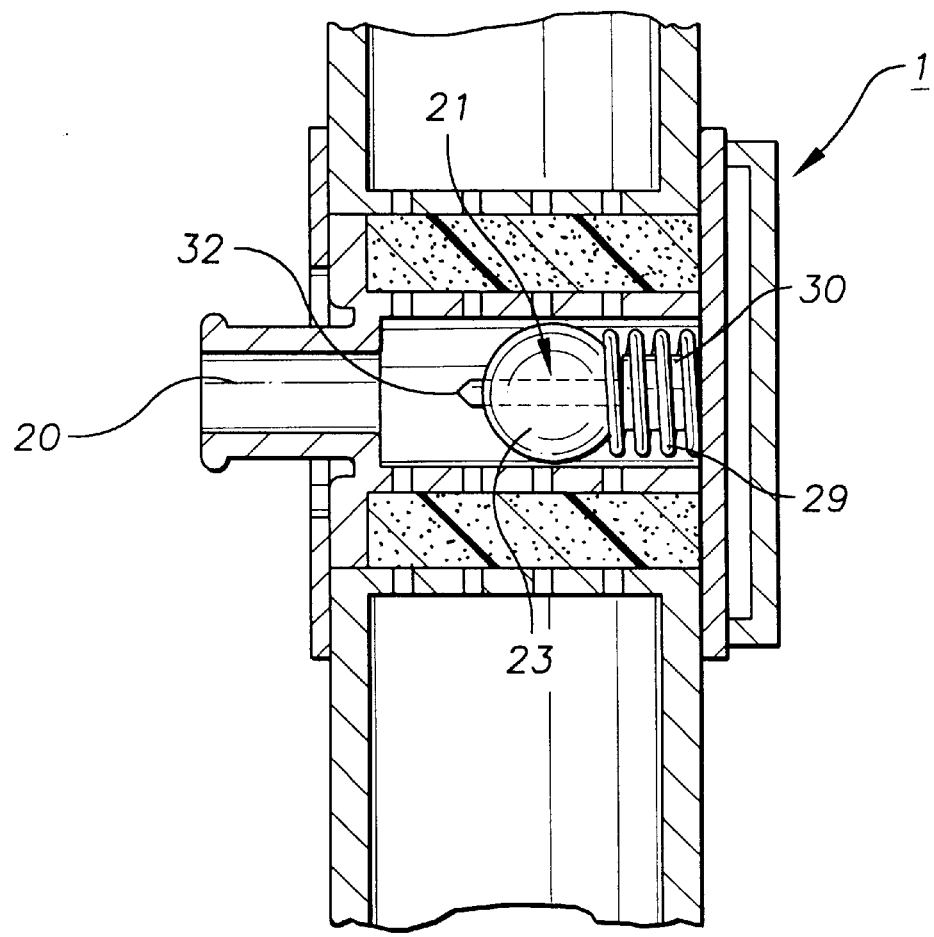
FIG. 3 is a side view of the central housing showing the embodiment of a compressed ball check spring and a plunger seated in the gas vent path.

FIG. 3 demonstrates the central subassembly 1 of the present invention wherein a tapered point plunger 32 is fixedly attached to the rear support collar 30 and penetrates the gas vent path 21 centrally located in the ball check 23. This action occurs during fecal matter entrance into the stoma connection 20 causing compression of the ball check spring 29, thereby preventing blockage of the gas vent path 21.

Figure 4:
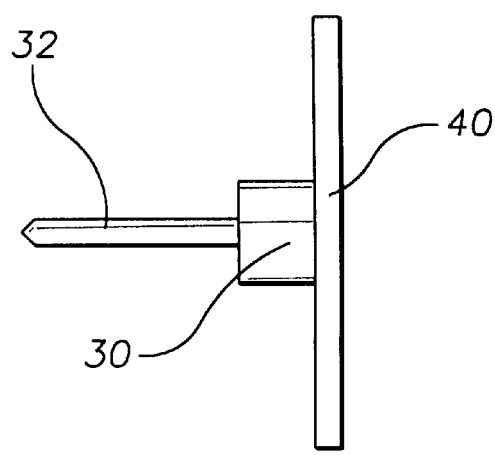
FIG. 4 is a side view of the plunger unit seated on the plunger base.

FIG. 4 shows the tapered point plunger 32 fixedly attached to the rear support collar 30, which is fixedly attached to the plunger base 40.

The preferred embodiments may be constructed of a variety of both flexible and/or hard plastics, with the ball check spring preferably made of teflon. The stool-collecting subassembly 3 and the gas-collecting subassembly 1 can be configured in a variety of shapes, any of which better accommodates waste and is comfortable to the user.

We claim:

1. A colostomy container capable of being attached to a stoma of a patient for purposes of sound-insulation and separation of flatus from stool evolving from a human digestive tract, comprising:

(a) a central subassembly, comprising:
    (i) a cylindrical housing having a back and an opposing front, said front having a circular opening;
    (ii) an open-cell polyurethane foam insulator circumferentially disposed around said cylindrical housing having a v-shaped cut-out section and having a plurality of perforations therein;
    (iii) a connecting tube protruding from said front whereby said flatus and said stool can exit said stoma and flow through said tube to said circular opening;
    (iv) a spherical ball-check having a back face and having a front face disposed against said circular opening and having a cylindrical hole bored through said spherical ball-check whereby said flatus coming into contact with said spherical ball-check enters said cylindrical hole at said front face and flows to said back face;
    (v) a plunger rod protruding from said back having a conical tip and an encircling solid base fixedly attached to said back of said cylindrical housing, said plunger rod disposed outside of and directly in line with said cylindrical hole whereby said flatus flows to said back face;
    (vi) a compression spring with a free end and a fixed end, said free end disposed against said back face, said fixed end connected to said back of said cylindrical housing, whereby said compression spring is uncompressed when said flatus comes into contact with said spherical ball-check allowing said flatus to exit said back face and enter said cylindrical housing and thereby flows through said perforations, and whereby said spring is actuated and compresses when said stool coming into contact with said spherical ball-check at said circular opening displaces said spherical ball-check towards said back thereby allowing said plunger rod to penetrate said spherical ball-check through said cylindrical hole thereby allowing said stool to enter said cylindrical housing and proceed to flow through said perforations without said stool clogging said cylindrical hole; and,
    (vii) a belt connector connected to said central subassembly as a means for securing said container to an individual;
  (b) a gas-collecting subassembly fixedly connected to said central subassembly and disposed upwardly from said central subassembly thereby receiving said flatus which exits said perforations, comprising:
    (i) an elongated, flexible chamber having a left end and a right end and a rounded top end, said left end and said right end adapted to flexibly bend, whereby said flexible chamber can conform to a user;
    (ii) a graphite filter having a planar lower face and a rounded upperface, said rounded upperface molded to fit and connect inside said rounded top end, whereby said flatus is filtered and deodorized and,
    (iii) a vent hole centrally located at said rounded top end directly above said filter enabling said flatus to exit said chamber;

c) a stool-collecting subassembly removably fastened to said central subassembly and disposed downwardly from said central subassembly, wherein said stool and said flatus enter, comprising:
- (i) an elongated, flexible tube chamber having a rounded left edge and a rounded right edge, and having a rounded bottom end and an open top end, said rounded left edge and said rounded right edge adapted to flexibly bend, whereby said flexible tube chamber can conform to said user; and,
- (ii) a means for removably fastening said open top end to said central subassembly, whereby said stool-collecting subassembly can be separately cleaned or disposed of.

2. A colostomy container as claimed in claim 1, further comprising an adhesive donut encircling said connecting tube and attached to said container as a means for securing said container to an individual.

* * * * *